United States Patent
Wollenweber et al.

(10) Patent No.: US 8,923,592 B2
(45) Date of Patent: Dec. 30, 2014

(54) METHODS AND SYSTEMS FOR PERFORMING ATTENUATION CORRECTION

(75) Inventors: Scott David Wollenweber, Waukesha, WI (US); Albert Henry Roger Lonn, Chalfont St Giles (GB)

(73) Assignee: General Electric Company, Schenectady, NY (US)

( * ) Notice: Subject to any disclaimer, the term of this patent is extended or adjusted under 35 U.S.C. 154(b) by 199 days.

(21) Appl. No.: 13/482,502

(22) Filed: May 29, 2012

(65) Prior Publication Data

US 2013/0322715 A1 Dec. 5, 2013

(51) Int. Cl.
*G06K 9/00* (2006.01)

(52) U.S. Cl.
USPC .......................................................... 382/131

(58) Field of Classification Search
USPC .......... 382/131, 133, 128, 168, 171, 224, 225
See application file for complete search history.

(56) References Cited

U.S. PATENT DOCUMENTS

| | | | |
|---|---|---|---|
| 7,729,467 B2 | 6/2010 | Kohlmyer et al. | |
| 7,813,783 B2 | 10/2010 | Thomas et al. | |
| 8,098,916 B2 | 1/2012 | Thielemans et al. | |
| 8,107,695 B2 | 1/2012 | Wollenweber | |
| 8,406,495 B2* | 3/2013 | Gagnon et al. | 382/128 |
| 2011/0123083 A1* | 5/2011 | Ojha et al. | 382/131 |
| 2013/0142411 A1* | 6/2013 | Da Silva et al. | 382/131 |
| 2013/0336564 A1* | 12/2013 | Hu et al. | 382/131 |

* cited by examiner

*Primary Examiner* — Yon Couso
(74) *Attorney, Agent, or Firm* — Dean D. Small; The Small Patent Law Group (57) ABSTRACT

A method for correcting a positron emission tomography (PET) image includes obtaining a magnetic resonance (MR) image dataset, classifying at least one object in the MR image as a bone, generating MR-derived PET attenuation correction factors based on the object classified as the bone, and attenuation correcting a plurality of positron emission tomography (PET) emission data using the MR-derived PET attenuation correction factors. A medical imaging system and a non-transitory computer readable medium are also described herein.

20 Claims, 10 Drawing Sheets

METHODS AND SYSTEMS FOR PERFORMING ATTENUATION CORRECTION

BACKGROUND OF THE INVENTION

The subject matter disclosed herein relates generally to imaging systems, and more particularly to a method and system for performing attenuation correction of medical images.

Multi-modality imaging systems scan using different modalities, for example, Computed Tomography (CT), Magnetic Resonance Imaging (MRI), Positron Emission Tomography (PET), and Single Photon Emission Computed Tomography (SPECT). During operation, image quality may be affected by various factors. One such factor is patient motion. Another factor is inaccurate attenuation correction between images acquired using two different imaging modalities caused by the patient motion.

Accordingly, at least one known PET-CT system utilizes data that is generated by the CT system to generate an attenuation correction of the PET scan data. Specifically, a plurality of emission attenuation correction factors are derived from CT data that is generated during a CT scan, wherein the CT system is specifically configured to generate data to be utilized for the CT attenuation correction factors. More specifically, the CT information is utilized to generate a linear attenuation map at 511 keV, which may then be applied to attenuation correct the PET information.

Moreover, at least one known PET-MR system utilizes data that is generated by the MR system to generate an attenuation correction of the PET scan data. However, utilizing the MR data to generate a linear attenuation map at 511 keV, which may then be applied to attenuation correct the PET information may result in unwanted artifacts or inaccurate PET quantitation and therefore may reduce the diagnostic value of images generated using the PET scan data.

BRIEF DESCRIPTION OF THE INVENTION

In one embodiment, a method for correcting a positron emission tomography (PET) image is provided. The method includes obtaining a magnetic resonance (MR) image dataset, classifying at least one object in the MR image as a bone, generating MR-derived PET attenuation correction factors based on the object classified as the bone, and attenuation correcting a plurality of positron emission tomography (PET) emission data using the MR-derived PET attenuation correction factors. A medical imaging system and a non-transitory computer readable medium are also described herein In another embodiment, a medical imaging system is provided. The medical imaging system includes a MRI system, a PET imaging system, and a computer coupled to the MRI system and the PET system. The computer is programmed to obtain a MR image dataset, classify at least one object in the MR image as a bone, generate MR-derived PET attenuation correction factors based on the object classified as the bone, and attenuation correct a plurality of positron emission tomography (PET) emission data using the MR-derived PET attenuation correction factors.

In a further embodiment, a non-transitory computer readable medium is provided. The non-transitory computer readable medium is encoded with a program programmed to instruct a computer to obtain a MR image dataset, classify at least one object in the MR image as a bone, generate MR-derived PET attenuation correction factors based on the object classified as the bone, and attenuation correct a plurality of positron emission tomography (PET) emission data using the MR-derived PET attenuation correction factors.

DETAILED DESCRIPTION OF THE INVENTION

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Figure 1:
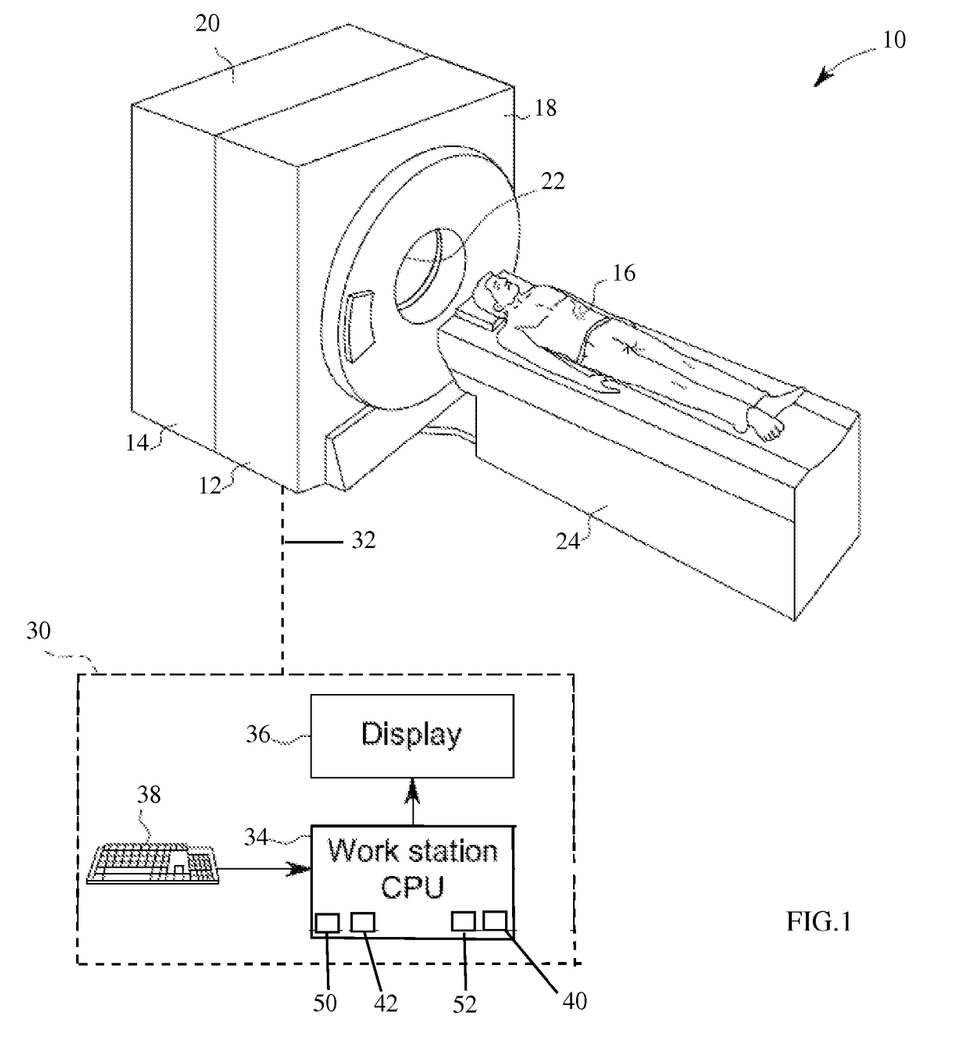
FIG. 1 is a pictorial view of an exemplary imaging system formed in accordance with various embodiments.

Various embodiments described herein provide an imaging system 10 as shown in FIG. 1. The imaging system 10 is a multi-modality imaging system that includes different types of imaging modalities, such as Positron Emission Tomography (PET), Single Photon Emission Computed Tomography (SPECT), Computed Tomography (CT), ultrasound, Magnetic Resonance Imaging (MRI) or any other system capable of generating diagnostic images. In the illustrated embodiment, the imaging system 10 is a PET/MRI system. It should be realized that the various embodiments are not limited to multi-modality medical imaging systems, but may be used on a single modality medical imaging system such as a stand-alone PET imaging system or a stand-alone MRI system, for example. Moreover, the various embodiments are not limited to medical imaging systems for imaging human subjects, but may include veterinary or non-medical systems for imaging non-human objects, etc.

Referring to FIG. 1, the multi-modality imaging system 10 includes a first modality unit 12 and a second modality unit 14. These units may be aligned along an axis, as shown in 10, or may co-habit a common space surrounding the patient such as having 14 inside 12 or vice versa. The two modality units enable the multi-modality imaging system 10 to scan an object or subject 16 in a first modality using the first modality unit 12 and to scan the subject 16 in a second modality using the second modality unit 14. The scans may optionally, in the co-habited modality case, be simultaneous. The multi-modality imaging system 10 allows for multiple scans in different modalities to facilitate an increased diagnostic capability over single modality systems. In the illustrated embodiment, the first modality 12 is a PET imaging system and the second modality 14 is a MRI system. The imaging system 10 is shown as including a gantry 18 that is associated with the PET imaging system 12 and a gantry 20 that is associated with the MRI system 14. During operation, the subject 16 is positioned within a central opening 22, defined through the imaging system 10, using, for example, a motorized table 24.

The imaging system 10 also includes an operator workstation 30. During operation, the motorized table 24 moves the subject 16 into the central opening 22 of the gantry 18 and/or 20 in response to one or more commands received from the operator workstation 30. The workstation 30 then operates the first and/or second modalities 12 and 14 to both scan the subject 16 and to acquire emission data and/or MRI data of the subject 16. The workstation 30 may be embodied as a personal computer (PC) that is positioned near the imaging system 10 and hard-wired to the imaging system 10 via a communication link 32. The workstation 30 may also be embodied as a portable computer such as a laptop computer or a hand-held computer that transmits information to, and receives information from the imaging system 10. Optionally, the communication link 32 may be a wireless communication link that enables information to be transmitted to and/or from the workstation 30 to the imaging system 10 wirelessly. In operation, the workstation 30 is configured to control the operation of the imaging system 10 in real-time. The workstation 30 is also programmed to perform medical image diagnostic acquisition and reconstruction processes described herein.

The operator workstation 30 includes a central processing unit (CPU) or computer 34, a display 36, and an input device 38. As used herein, the term "computer" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. The above examples are exemplary only, and are thus not intended to limit in any way the definition and/or meaning of the term "computer". In the exemplary embodiment, the computer 34 executes a set of instructions that are stored in one or more storage elements or memories, in order to process information received from the first and second modalities 12 and 14. The storage elements may also store data or other information as desired or needed. The storage element may be in the form of an information source or a physical memory element located within the computer 34.

The imaging system 10 also includes an attenuation correction module 40 that is configured to implement various methods described herein. In general, in many areas of the human body, bone density may be modeled as a dense outer shell having a less dense inner core, depending on the location and size of the bone structure. For example, the human skull tends to have a larger density but thinner total dimension. Whereas, a pelvic bone, a femoral bone, the spinal cord, and/or other large bone structures may have a dense outer shell, but also may have marrow in the center core with a lower overall density. Accordingly, for MR-based attenuation correction of 511 keV PET data, the attenuation correction module 40 is configured to estimate the linear attenuation coefficient for 511 keV gamma rays for at least one of the bones in the MRI image. More specifically, the attenuation correction module 40 is configured to convert the MR images based upon classification of different image features, such as, for example, a bone as is described in more detail below.

The attenuation correction module 40 may be implemented as a piece of hardware that is installed in the computer 34. Optionally, the attenuation correction module 40 may be implemented as a set of instructions that are installed on the computer 34. The set of instructions may be stand alone programs, may be incorporated as subroutines in an operating system installed on the computer 34, may be functions in an installed software package on the computer 34, and the like. It should be understood that the various embodiments are not limited to the arrangements and instrumentality shown in the drawings.

The set of instructions may include various commands that instruct the computer 34 as a processing machine to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 2:
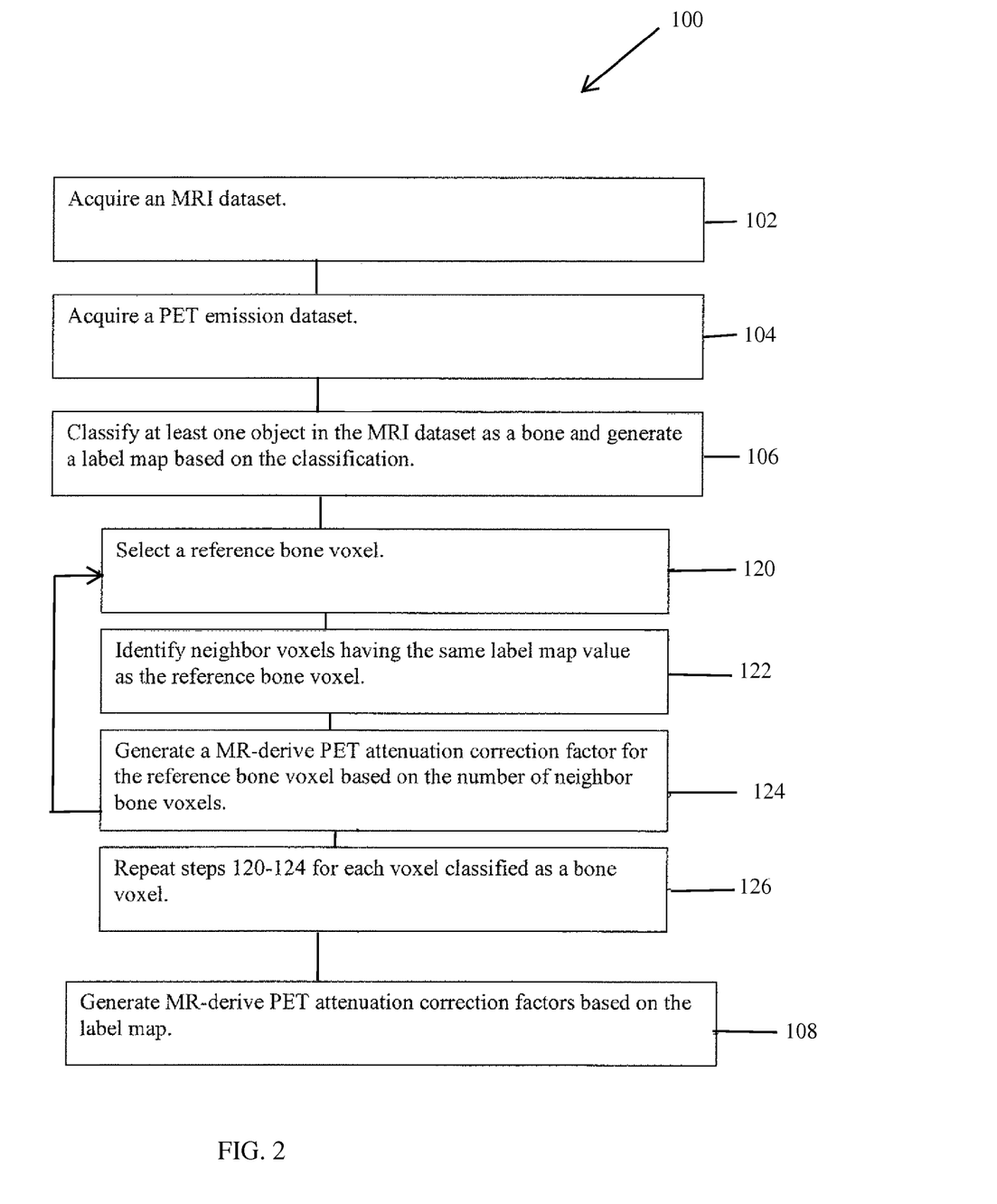
FIG. 2 is a flowchart illustrating a method for attenuation correcting positron emission tomography (PET) emission data in accordance with various embodiments.
Figure 3:
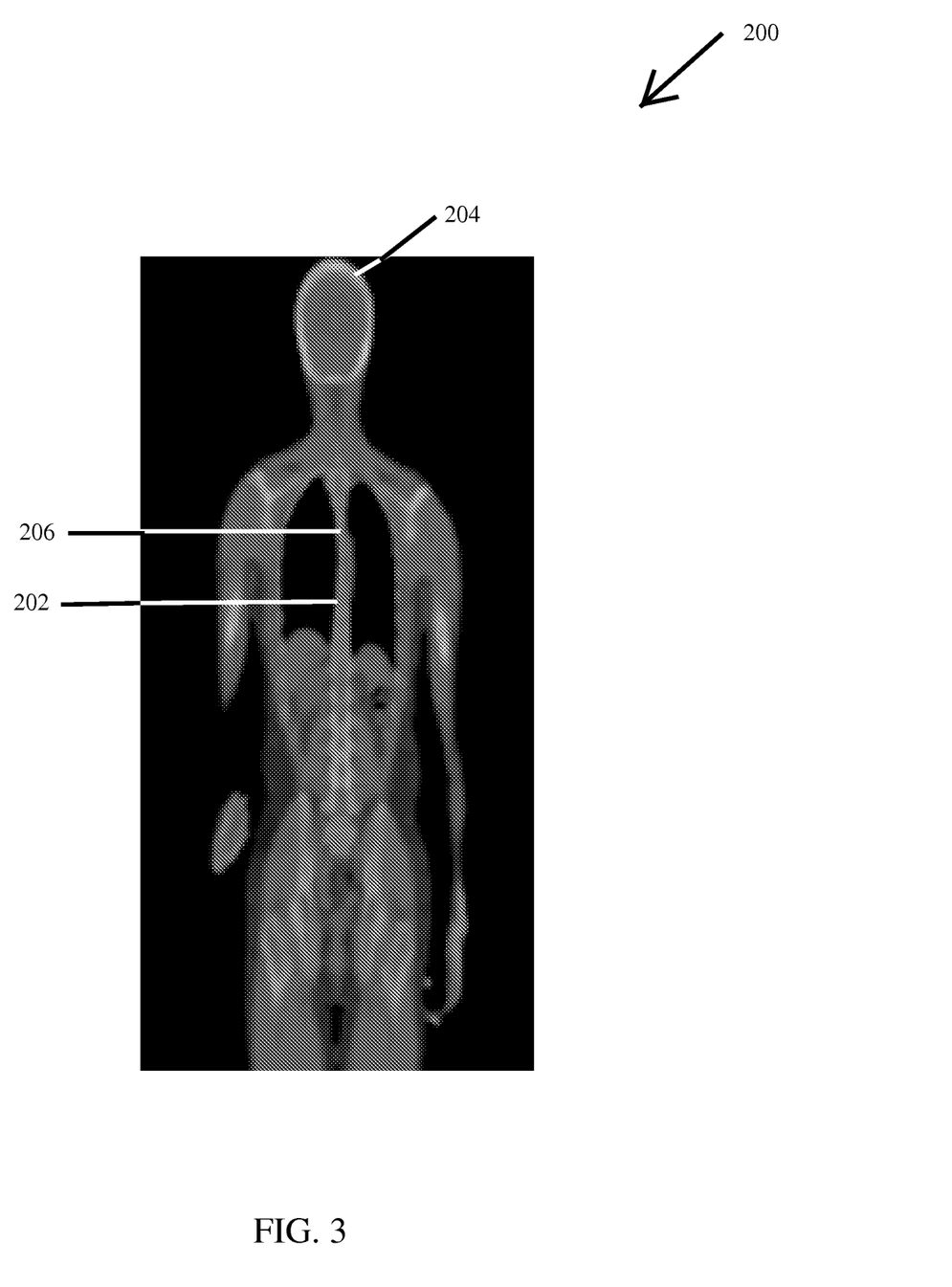
FIG. 3 is an exemplary image that may be generated in accordance with various embodiments.

FIG. 2 is a flowchart of an exemplary method 100 for attenuation correcting PET emission data. In various embodiments, the method 100 may be implemented using for example, the computer 34 and/or the attenuation correction module 40. At 102, an MRI dataset 50 is acquired using, for example, the MRI system 14 shown in FIG. 1. The MRI dataset 50 may be obtained by performing a scan of the subject 16 to produce the MRI dataset 50. Optionally, the MRI dataset 50 may be obtained from data collected during a previous scan of the subject 16, wherein the MRI dataset 50 has been stored in a memory device, such as a memory device 42 (shown in FIG. 1). The MRI dataset 50 may be stored in any format. The MRI dataset 50 may be obtained during real-time scanning of the subject 16. For example, the methods described herein may be performed on MRI data as the MRI dataset 50 is received from the MRI system 14 during a real-time examination of the subject 16. In various embodiments, the MRI dataset 50 includes at least one bone. For example, FIG. 3 is an exemplary image 200 of the subject 16, including an exemplary object 202. In various embodiments, the object 202 may be a first bone type or classification 204 which has a substantially uniform density, such as for example, a skull bone. In various other embodiments, the object 202 may be a second bone type or classification 206 bone having an exterior portion having a higher density, and an interior portion having a lower density than the exterior portion, such as for example, a femur, a pelvic bone, etc.

At 104, a PET emission dataset 52, or sinograms, are acquired using, for example, the PET system 12 shown in FIG. 1. The PET emission dataset 52 may be obtained by performing a scan of the subject 16 to produce the PET emission dataset 52. Optionally, the PET emission dataset 52 may be obtained from data collected during a previous scan of the subject 16, wherein the PET emission dataset 52 has been stored in a memory device, such as a memory device 42 (shown in FIG. 1). The PET emission dataset 52 may be stored in any format. The PET emission dataset 52 may be obtained during real-time scanning of the subject 16. For example, the methods described herein may be performed on PET emission data as the PET emission dataset 52 is received from the PET system 12 during a real-time examination of the subject 16.

At 106, at least one object 202 in the MRI dataset 50 is classified as a bone. More specifically, and as shown in FIG. 3, the voxels representing the object 202 have a higher intensity and thus appear as brighter voxels. Whereas, soft tissue, organs, etc., surrounding the object 202, have a lower density and thus appear as darker voxels. Accordingly, in various embodiments, to classify the object 202 as a bone, an intensity based segmentation is performed on the MRI dataset 50. In operation, a segmentation algorithm, which may be installed on the attenuation correction module 40, is configured to locate objects of interest, such as the bone 202, and separate image data of the bone 202 from image data of surrounding objects of lesser or no interest.

The segmentation algorithm uses a principle, whereby it is generally assumed that the object 202 may be differentiated from other anatomical features by determining the intensity of each voxel in the image data. Based on the intensity values of each of the voxels, the bone 202 may be distinguished from the other anatomical features. Accordingly, at 106 the segmentation algorithm automatically compares the intensity values for each voxel in the MRI dataset 50 to a predetermined intensity value, using for example, a thresholding process. In the exemplary embodiment, the predetermined intensity value may be a range of predetermined intensity values. The predetermined intensity value range may be automatically set based on a priori information of the bone, for example. Optionally, the predetermined range may be manually input by the operator. In one embodiment, if the intensity value of a voxel representing the object 202 is within the predetermined range, the voxel is classified as bone. Otherwise, the voxel is classified as not belonging to the bone. It should be realized that the segmentation algorithm may also be utilized with other segmentation techniques to identify the bone. Additionally, as should be appreciated, other suitable segmentation algorithms may be used.

Figures 4, 5:
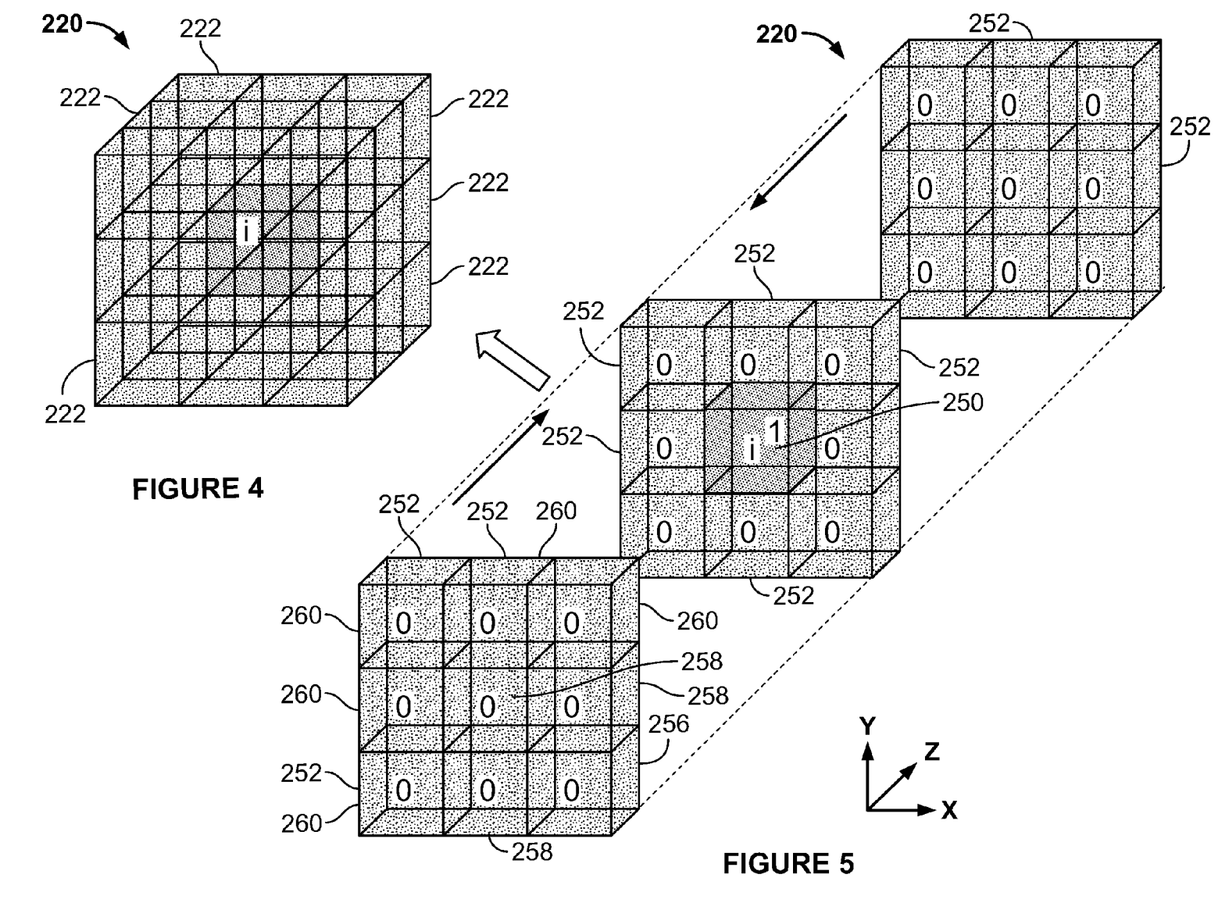
FIG. 4 is a portion of a density map that may be generated in accordance with various embodiments.
FIG. 5 is an exploded view of the density map shown in FIG. 4.

In various embodiments, the image data in the MRI dataset 50, for example, voxel information that is identified using the segmentation algorithm, may be utilized to generate a three-dimensional density map, also referred to herein as a label map, wherein voxels identified as bone are assigned a first label map value, and voxels that are not bone are assigned a second label map value. For example, FIG. 4 illustrates a portion of an exemplary three-dimensional (3D) density map 220 that may be generated at 106 and FIG. 5 is an exploded view of the label map 220 shown in FIG. 4. In the illustrated embodiments, the density map 220 includes twenty-seven voxels 222. More specifically, the density map 220 illustrates a central voxel i that is surrounded by twenty-six voxels. In the illustrated embodiment, the twenty-six voxels are adjacent to the voxel i and are therefore referred to herein as "neighbors". It should be appreciated that in operation, the density map 220 may include thousands of voxels 222 and twenty-seven voxels 222 are shown to explain various embodiments described herein. In the illustrated embodiment, the voxels 222 identified as bone are assigned a first label map value, such as 1, and the voxels 222 that are not bone are assigned a second label map value, such as 0. Accordingly, in various embodiments, the object 202 may be classified as a bone by performing a segmentation of the MRI dataset 50 and assigning each voxel 222 a label map value that indicates that the voxel 222 is either bone or not bone.

Additionally, in various embodiments, the object 202 may be classified as a bone by manually comparing the object 202 to a plurality of images in an atlas. An atlas, as used herein, is a electronic or hardcopy file that includes one or more images of various portions of the human anatomy. Accordingly, in operation, the user may manually observe the object 202 and manually locate an image within the atlas that is substantially the same as the observed object. In various other embodiments, the object 202 may be classified as a bone based on a priori knowledge. More specifically, the operator may have a priori knowledge based on the operator's experience that the object 202 is a skull, a femur, etc. The label map values may then be manually entered into the density map 200 by the operator.

Referring again to FIG. 2, at 108, MR-derived PET attenuation correction factors are generated based on the label map values assigned at 106. In various embodiments, generating MR-derived PET attenuation correction factors includes selecting at 120 a reference bone voxel, identifying at 122 neighbor voxels having the same label map value as a reference bone voxel, and generating at 124 a MR-derived PET attenuation correction factor for the reference bone voxel based on the number of neighbor bone voxels. At 126, steps 120-124 are repeated for each voxel classified as bone in the MRI dataset 50. The attenuation correction factors are then utilized to attenuation correct the PET images.

More specifically, as discussed above, large bones often have a dense compact bone shell surrounding a lower density trabecular bone center with a mixture of bone and marrow. Accordingly, the interior of the bone may be distinguished from the exterior of the bone by selecting a reference bone voxel and then calculating a quantity of neighbor voxels, e.g. adjacent voxels that are also classified as bone based on the label map values assigned at 106. In general, a "surface" bone portion is assigned a higher density value and an "interior" bone portion is assigned a lower density value for use during PET attenuation correction.

For example, and referring again to FIGS. 4 and 5 a reference bone voxel 250, such as the voxel i, is initially selected. In the illustrated embodiment, the reference bone voxel 250 has been previously identified and assigned a label map value of 1, as described above. Each of the neighbor voxels 252 or connected voxels are then identified. Neighbor, as used herein, means a voxel that is adjacent to the reference bone voxel 250 in an x-direction, a y-direction, and a z-direction. Accordingly, in the illustrated embodiment, the reference bone voxel 250 has twenty-six neighbor voxels 252. However, it should be realized that the method described herein may be implemented with more than twenty-six neighbor voxels. For example, various connected voxels may also be selected. Connected voxel, as used herein, means a voxel that is adjacent to a neighbor voxel. For example, and referring to FIG. 4, assume that a voxel 256 is selected as a reference voxel, then voxels 258 would be neighbor voxels and voxels 260 would be a connected voxel. It should be appreciated that the neighbor voxels 252 may be positioned in each of the x-direction, the y-direction, and the z-direction from the reference voxel 250. Moreover, the connected voxels, such as the voxels 260 may also be positioned in each of the x-direction, the y-direction, and the z-direction from the reference voxel 250. Accordingly, in the illustrated embodiment, the neighbor voxels 252 represent a 3×3×3 box of neighbor voxels 252 that surround the reference bone voxel 250.

After the neighbor voxels 252 and/or connected voxels are identified, the neighbor voxels 252 and/or connected voxels classified as bone voxels are counted at 122. More specifically, neighbor voxels 252 having a label map value of 1 are counted. In the illustrated embodiment of FIGS. 4 and 5, the reference bone voxel 250 has twenty-six neighbor voxels 252. Moreover, twenty-five of the neighbor voxels 252 are classified as non-bone voxels (0) and are therefore not counted. Accordingly, in the embodiment illustrated in FIGS. 4 and 5, because all the neighbor voxels 252 are not bone, this signifies that the reference voxel 250 and the neighbor voxels 252 represent a 'stand-alone' bone voxel, and hence the attenuation correction factor, i.e., a density value assigned to the reference voxel 250 is left at a default density value.

Figures 6, 7:
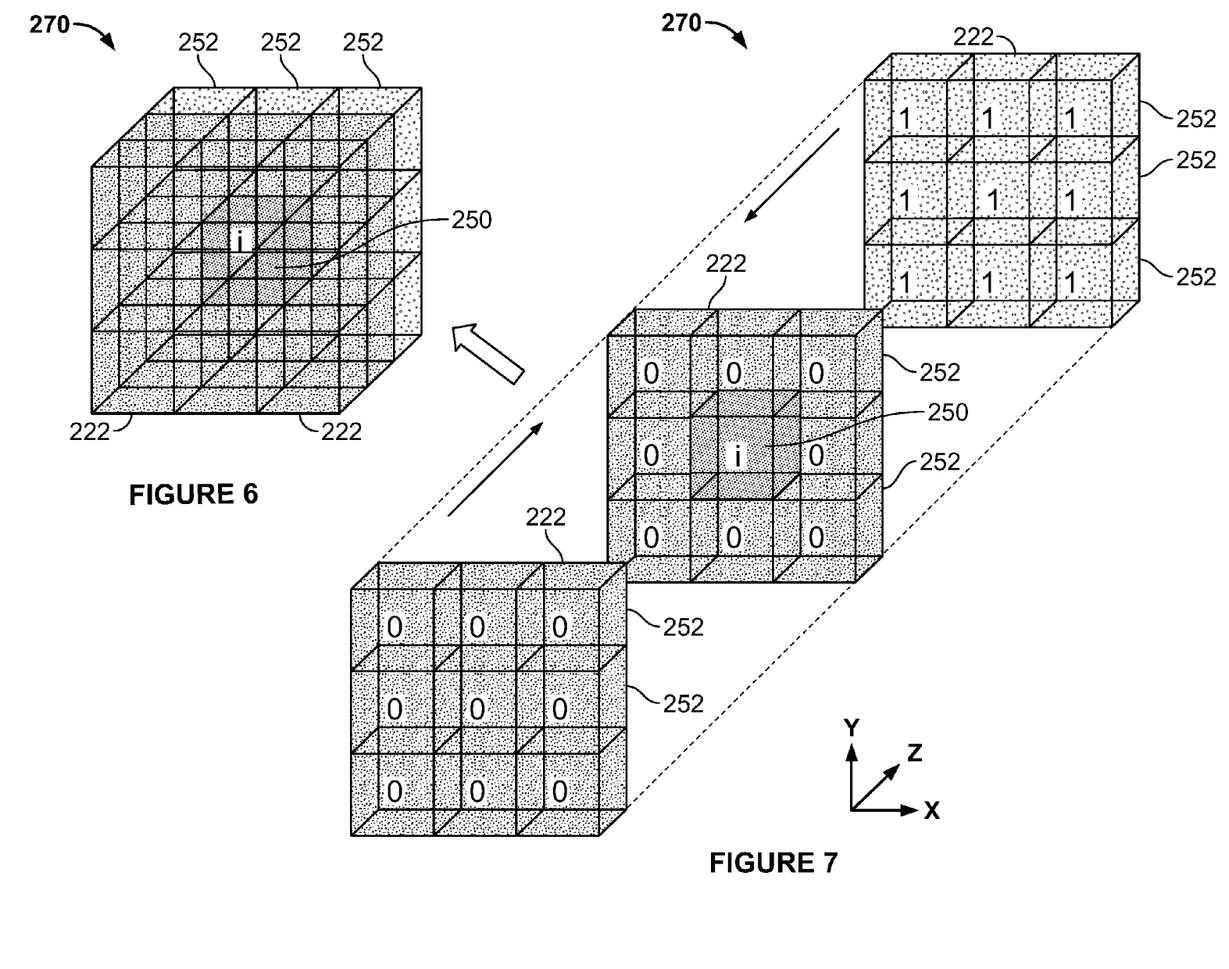
FIG. 6 is a portion of another density map that may be generated in accordance with various embodiments.
FIG. 7 is an exploded view of the density map shown in FIG. 6.

FIG. 6 illustrates a portion of another exemplary three-dimensional (3D) density map 270 that may be generated at 106 and FIG. 7 is an exploded view of the label map 270 shown in FIG. 6. In the illustrated embodiment, the density map 270 includes twenty-seven voxels 222 wherein the reference voxel 250 again has twenty-six neighbor voxels 252. Moreover, nine of the neighbor voxels 252 are classified as bone voxels (1) and seventeen of the neighbor voxels 252 are classified as non-bone voxels and are therefore not counted. Accordingly, in the embodiment illustrated in FIGS. 6 and 7, because the distribution of the neighbor voxels 252 exhibits reference voxel 250 as an edge voxel, the reference voxel 250 is assigned an attenuation correction factor, i.e., a density value, that is higher than the intensity value assigned to the reference voxel 250 in FIGS. 4 and 5. It should be realized that the density value assigned to the reference voxel 250 is based on the quantity and distribution of neighbor voxels 250 that are classified as bone. For example, assume that the density value assigned to reference pixel is between a range of 0 and 1. Thus, if none of the neighbor voxels 252 are classified as bone, the density value assigned to the reference voxel is 1. Optionally, if all the neighbor voxels 252 are classified as bone, the density value assigned to the reference voxel is decreased. Accordingly, the reference voxel 250 is assigned a density value based on the quantity of neighbor voxels 252 and/or connected voxels that are classified as bone. Thus, the embodiment illustrated in FIGS. 6 and 7 because nine of the neighbor voxels 252 are classified as bone and are in one direction from reference voxel 250, the density value assigned to the reference voxel 250 may be increased for example, approximately 1.3.

Figures 8, 9:
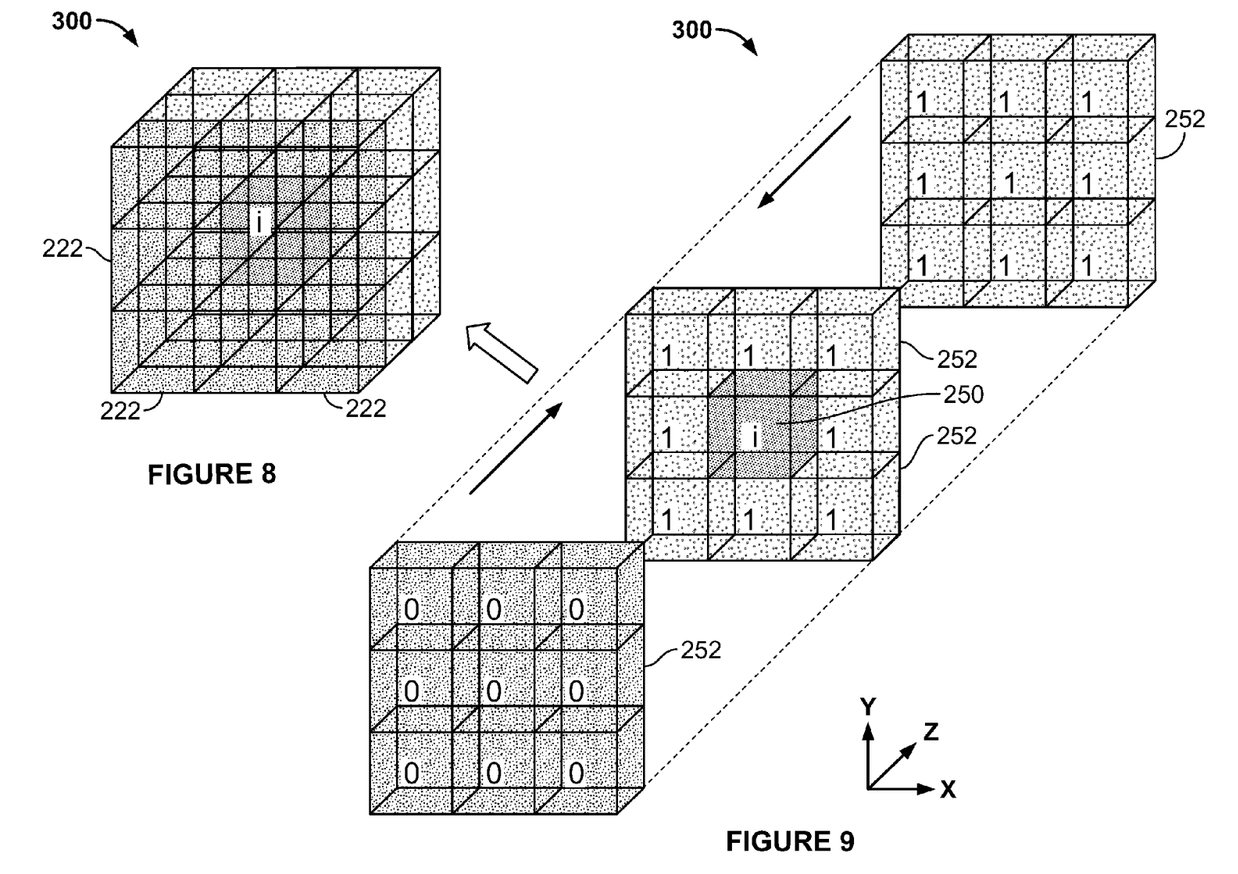
FIG. 8 is a portion of another density map that may be generated in accordance with various embodiments.
FIG. 9 is an exploded view of the density map shown in FIG. 8.

FIG. 8 illustrates a portion of another exemplary three-dimensional (3D) density map 300 that may be generated at 106 and FIG. 9 is an exploded view of the label map 300 shown in FIG. 8. In the illustrated embodiment, the density map 300 includes twenty-seven voxels 222 wherein the reference voxel 250 again has twenty-six neighbor voxels 252. Moreover, seventeen of the neighbor voxels 252 are classified as bone voxels (1) and nine of the neighbor voxels 252 are classified as non-bone voxels and are therefore not counted. In this example, as compared to the example in FIGS. 6 and 7, the reference voxel 250 is less 'exterior' to the bone, and for example may have a density value assigned as 1.1 of the default bone attenuation correction factor value.

Figures 10, 11:
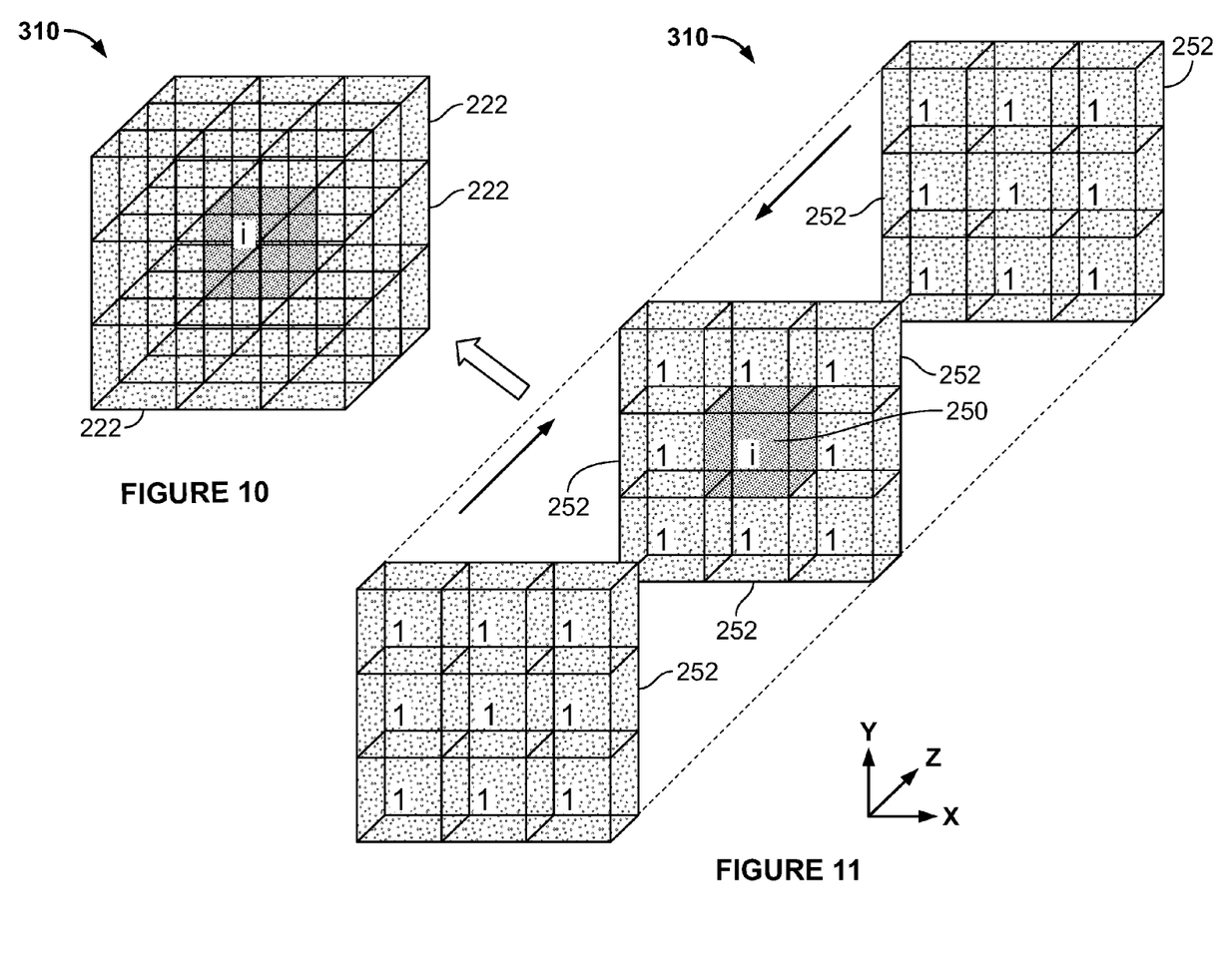
FIG. 10 is a portion of still another density map that may be generated in accordance with various embodiments.
FIG. 11 is an exploded view of the density map shown in FIG. 10.

FIG. 10 illustrates a portion of another exemplary three-dimensional (3D) density map 310 that may be generated at 106 and FIG. 11 is an exploded view of the label map 310 shown in FIG. 10. In the illustrated embodiment, the density map 310 includes twenty-seven voxels 222 wherein the reference voxel 250 again has twenty-six neighbor voxels 252. Moreover, twenty-six of the neighbor voxels 252 are classified as bone voxels (1) and none of the neighbor voxels 252 are classified as non-bone voxels and are therefore not counted. Accordingly, in the embodiment illustrated in FIGS. 10 and 11, because all of the neighbor voxels 252 are classified as bone, i.e. approximately 100%, the density value assigned to the reference voxel 250 may be decreased for example, approximately 0.9 of the default bone attenuation correction factor value.

Figure 12:
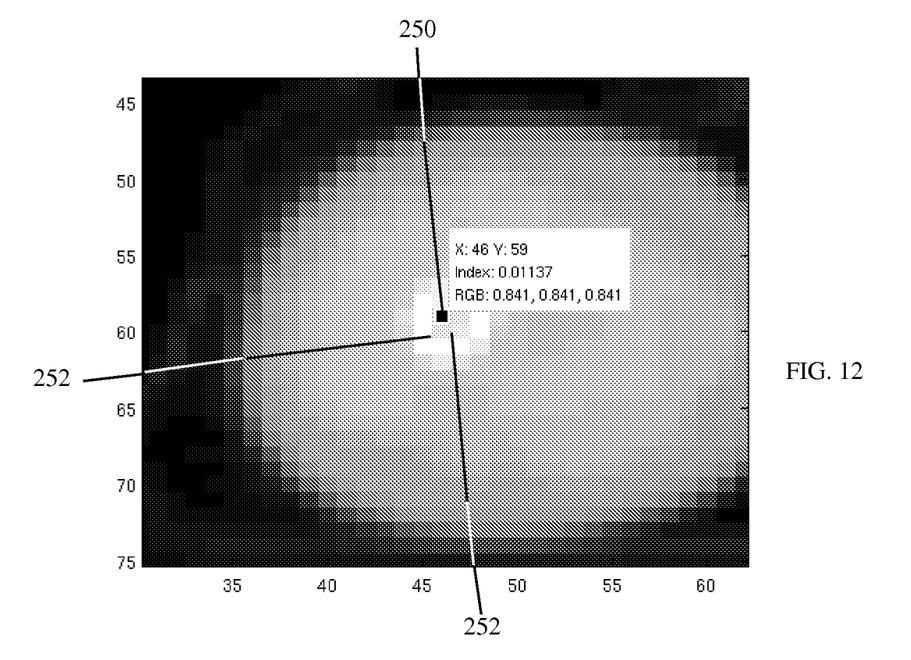
FIG. 12 is an attenuation correction map that may be generated in accordance with various embodiments.

In general, the methods described herein are configured to identify interior and exterior bone voxels by counting the number of neighbor voxels that are the same, e.g. are bone voxels. For example, if a reference bone voxel is bone, a determination is made as to how many neighbor voxels are also bone. Accordingly, in various embodiments, the attenuation may be modulated based on the number of neighbor voxels that are classified as bone. In one embodiment, if all the neighbor voxels 252 are bone, this signifies that the reference voxel 250 and the neighbor voxels 252 represent an interior portion of the bone and are assigned a lower attenuation correction factor. For example, FIG. 12 is an exemplary attenuation correction map 320 that illustrates the reference voxel 250 and the nearest neighbor voxels 252. As shown in FIG. 12, the reference voxel 250 is substantially surrounded by neighbor voxels that are also bone. Thus, the reference voxel 250 is located in the interior portion of the bone and is assigned a lower attenuation correction factor.

Figure 13:
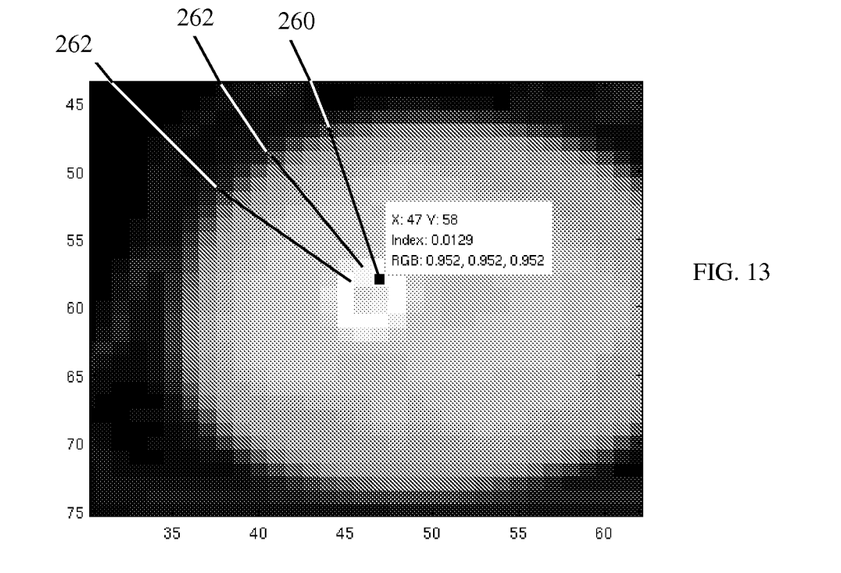
FIG. 13 is another attenuation correction map that may be generated in accordance with various embodiments.

However, in other embodiments, if approximately half of the neighbor voxels 252 are bone voxels and the other half are not bone voxels and the distribution of bone/not bone has the shape of an edge surface (0/1 are distributed left/right, up/down, etc.), the reference bone voxel is assigned a higher attenuation correction factor. For example, FIG. 13 is an exemplary attenuation correction map 330 that illustrates a reference voxel 260 and the nearest neighbor voxels 262 wherein approximately half the nearest neighbor voxels 262 are bone voxels and half are not bone voxels. Thus, the reference voxel 260 is located in the exterior portion of the bone and is assigned a higher attenuation correction factor. The attenuation correction factor is based on the quantity of neighboring voxels identified as bone. In various embodiments, the attenuation correction factor may be within a predetermined range. For example, in one embodiment, if all of the nearest neighbor voxels are bone voxels, the reference bone voxel may be assigned an attenuation correction factor of 0.9 of the default bone attenuation correction factor value. Optionally, if only one of the neighbor voxels is a bone voxel, the reference bone voxel may be assigned an attenuation correction factor of approximately 1. In various embodiments, the attenuation correction factor sealing assigned to each reference voxel is based upon a linear scale of between, for example, 0 and 1. Thus, if half the neighbor voxels are bone voxels and are distributed in one direction from the reference voxel, and half the neighbor voxels are not bone voxels and distributed in the opposite direction from the reference voxel, the reference bone voxel may be assigned an attenuation correction scaling factor of approximately 1.1.

Described herein are methods and systems that utilize MR information to provide attenuation correction of PET images. More specifically, various embodiments identify thicker bones generally having a "soft" (lower attenuation) center of marrow (spine, pelvis). In operation, MR images are utilized to find the bone class. The number of neighbor voxels within the bone class for each voxel classified as bone is then determined. A lower attenuation correction factor is assigned to bone voxels based upon an increasing or fixed large number of neighbor voxels since the more internal a voxel identified as bone is, the more likely that the voxel is less dense for some types of human bone. It should be realized that the methods described herein may also be run "backwards". More specifically, a reference non-bone voxel may be identified in the MR image dataset, a number and distribution of neighbor non-bone voxels for the reference bone voxel may be counted, a MR-derived PET attenuation correction factor scaling for the reference non-bone bone voxel based on the number and distribution of neighbor non-bone voxels may be generated generating; and a MR-derived PET attenuation correction factor scaling for the reference non-bone voxel based on the number and distribution of neighbor non-bone voxels may be generated.

Figure 14:
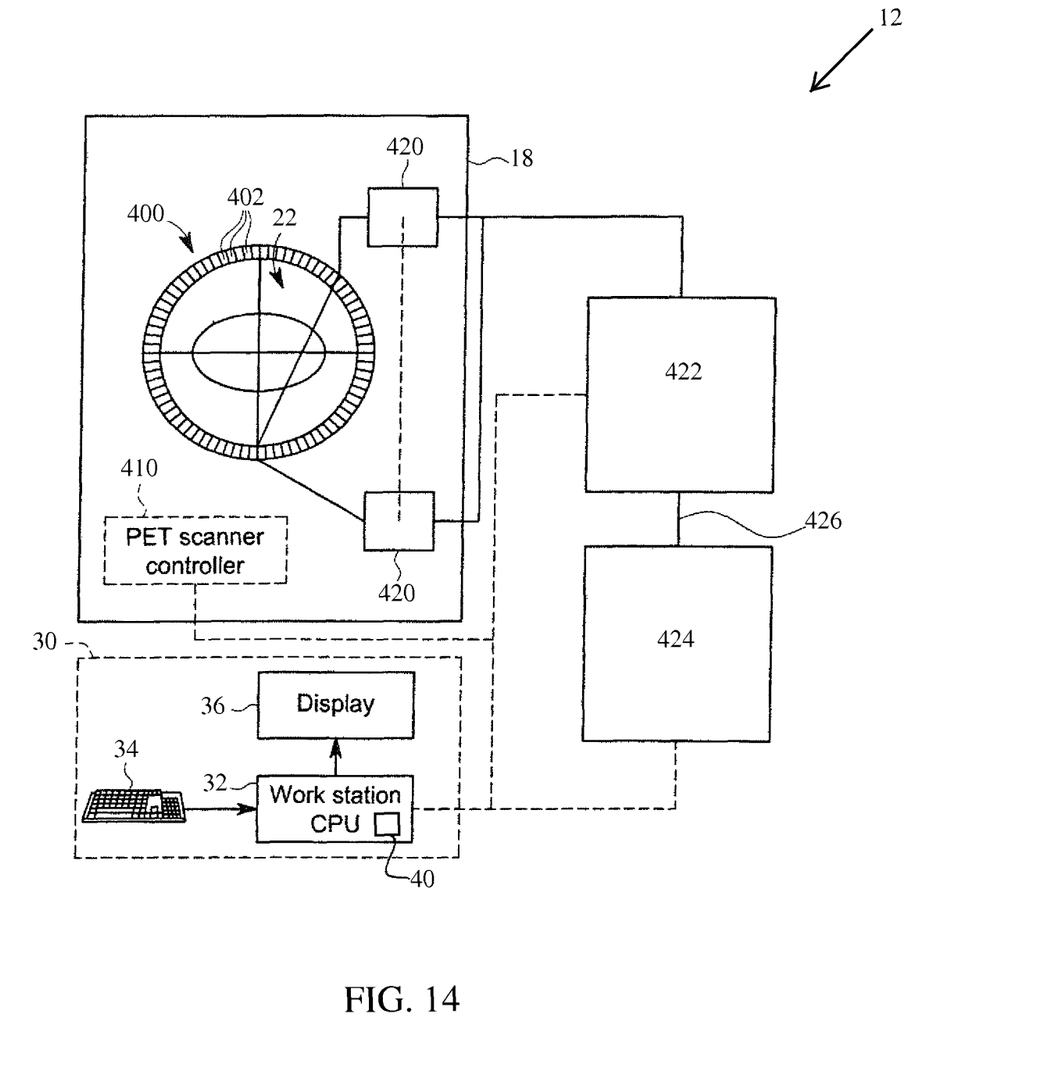
FIG. 14 is a block schematic diagram of the first modality unit shown in FIG. 1 in accordance with various embodiments.
Figure 15:
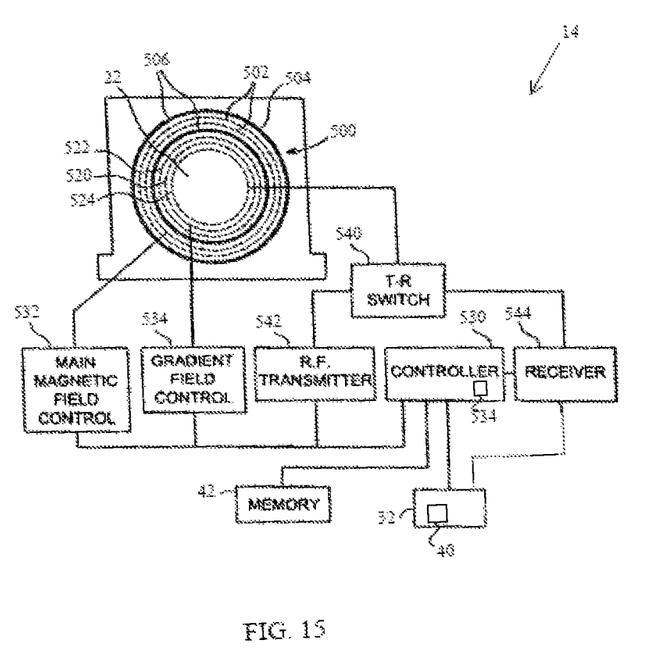
FIG. 15 is a block schematic diagram of the second modality unit shown in FIG. 1 in accordance with various embodiments.

Various embodiments of the methods described herein may be provided as part of, or used with, a medical imaging system, such as a dual-modality imaging system 10 as shown in FIG. 1. FIG. 14 is a block schematic diagram of the first modality unit 12, e.g. the PET imaging system, shown in FIG. 1. FIG. 15 is a block schematic diagram of the second modality unit 14, e.g. the MRI system, shown in FIG. 1.

As shown in FIG. 14, the PET system 12 includes a detector array 400 that is arranged as ring assembly of individual detector modules 402. The detector array 10 also includes the central opening 22, in which an object or patient, such as the subject 16 may be positioned, using, for example, the motorized table 24 (shown in FIG. 1). The motorized table 24 is aligned with the central axis of the detector array 400. During operation, the motorized table 24 moves the subject 16 into the central opening 22 of the detector array 400 in response to one or more commands received from the operator workstation 30. More specifically, a PET scanner controller 410 responds to the commands received from the operator workstation 30 through the communication link 32. Therefore, the scanning operation is controlled from the operator workstation 30 through PET scanner controller 410.

During operation, when a photon collides with a scintillator on the detector array 400, the photon collision produces a scintilla on the scintillator. The scintillator produces an analog signal that is transmitted to an electronics section (not shown) that may form part of the detector array 400. The electronics section outputs an analog signal when a scintillation event occurs. A set of acquisition circuits 420 is provided to receive these analog signals. The acquisition circuits 420 process the analog signals to identify each valid event and provide a set of digital numbers or values indicative of the identified event. For example, this information indicates when the event took place and the position of the scintillation scintillator that detected the event.

The digital signals are transmitted through a communication link, for example, a cable, to a data acquisition controller 422. The data acquisition processor 422 is adapted to perform the scatter correction and/or various other operations based on the received signals. The PET system 12 may also include an image reconstruction processor 424 that is interconnected via a communication link 426 to the data acquisition controller 422. During operation, the image reconstruction processor 424 performs various image enhancing techniques on the digital signals and generates an image of the subject 16.

As shown in FIG. 15 the MRI system 14 includes a superconducting magnet assembly 500 that includes a superconducting magnet 502. The superconducting magnet 502 is formed from a plurality of magnetic coils supported on a magnet coil support or coil former. In one embodiment, the superconducting magnet assembly 500 may also include a thermal shield 504. A vessel 506 (also referred to as a cryostat) surrounds the superconducting magnet 502, and the thermal shield 504 surrounds the vessel 506. The vessel 506 is typically filled with liquid helium to cool the coils of the superconducting magnet 502. A thermal insulation (not shown) may be provided surrounding the outer surface of the vessel 506. The MRI system 14 also includes a main gradient coil 520, a shield gradient coil 522, and an RF transmit coil 524. The MRI system 14 also generally includes a controller 530, a main magnetic field control 532, a gradient field control 534, the memory device 42, the display device 36, a transmit-receive (T-R) switch 540, an RF transmitter 542 and a receiver 544.

In operation, a body of an object, such as the subject 16 (shown in FIG. 1) is placed in the opening 22 on a suitable support, for example, the motorized table 24 (shown in FIG. 1). The superconducting magnet 502 produces a uniform and static main magnetic field $B_0$ across the opening 22. The strength of the electromagnetic field in the opening 22 and correspondingly in the patient, is controlled by the controller 530 via the main magnetic field control 532, which also controls a supply of energizing current to the superconducting magnet 502.

The main gradient coil 520, which may include one or more gradient coil elements, is provided so that a magnetic gradient can be imposed on the magnetic field $B_0$ in the opening 22 in any one or more of three orthogonal directions x, y, and z. The main gradient coil 520 is energized by the gradient field control 534 and is also controlled by the controller 530.

The RF coil assembly 524 is arranged to transmit magnetic pulses and/or optionally simultaneously detect MR signals from the patient, if receive coil elements are also provided. The RF coil assembly 524 may be selectably interconnected to one of the RF transmitter 542 or receiver 544, respectively, by the T-R switch 540. The RF transmitter 542 and T-R switch 540 are controlled by the controller 530 such that RF field pulses or signals are generated by the RF transmitter 542 and selectively applied to the patient for excitation of magnetic resonance in the patient.

Following application of the RF pulses, the T-R switch 540 is again actuated to decouple the RF coil assembly 524 from the RF transmitter 542. The detected MR signals are in turn communicated to the controller 530. The controller 530 may include a processor 554 that controls the processing of the MR signals to produce signals representative of an image of the subject 16. The processed signals representative of the image are also transmitted to the display device 36 to provide a visual display of the image. Specifically, the MR signals fill or form a k-space that is Fourier transformed to obtain a viewable image which may be viewed on the display device 36.

As used herein, a set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A method for correcting a positron emission tomography (PET) image, said method comprising:
   using one or more processors to obtain a magnetic resonance (MR) image dataset;
   classifying, using the one or more processors, at least one object in the MR image as a bone;
   identifying, using the one or more processors, a reference bone voxel in the MR image dataset;
   counting, using the one or more processors, a number and distribution of neighbor bone voxels for the reference bone voxel;
   generating, using the one or more processors, a MR-derived PET attenuation correction factor scaling for the reference bone voxel based on the number and distribution of neighbor bone voxels; and
   attenuation correcting a plurality of PET emission data using the MR-derived PET attenuation correction factors.

2. The method of claim 1, wherein classifying the object further comprises performing an intensity based segmentation of the MR image dataset to identify the bone.

3. The method of claim 1, wherein classifying the object further comprises:
   comparing the object to a plurality of images in an atlas; and
   classifying the bone based on the comparison.

4. The method of claim 1, wherein the MR image dataset comprises a plurality of voxels, said classifying the object further comprises:
   assigning a first label map value to voxels representing bone; and
   assigning a second label map value to voxels that are not bone.

5. The method of claim 1, wherein generating MR-derived PET attenuation correction factors further comprises:
   counting, using the one or more processors, a number and distribution of connecting bone voxels for the reference bone voxel; and
   wherein the MR-derived PET attenuation correction factor scaling for the reference bone voxel is further based on the number and distribution of connecting bone voxels.

6. The method of claim 1, wherein generating MR-derived PET attenuation correction factors further comprises:
   assigning a label map value to voxels representing bone;
   identifying neighbor voxels, and a relative distribution of the neighbor voxels, having the same label map value as a reference bone voxel; and
   generating a MR-derived PET attenuation correction factor for the reference bone voxel based on the number and distribution of neighbor bone voxels.

7. The method of claim 1, further comprising:
   determining, using the one or more processors, a number and distribution of neighbor bone voxels around a reference bone voxel; and
   generating, using the one or more processors, the MR-derived PET attenuation correction factors scaling based on the determined number and distribution of neighbor bone voxels.

8. A medical imaging system comprising:
   a magnetic resonance imaging (MRI) system;
   a positron emission tomography (PET) imaging system; and a computer coupled to the MRI system and the PET system, said computer being programmed to:
obtain a MR image dataset;
classify at least one object in the MR image as a bone;
identify a reference bone voxel in the MR image dataset;
count a number and distribution of neighbor bone voxels for the reference bone voxel;
generate a MR-derived PET attenuation correction factor scaling for the reference bone voxel based on the number and distribution of neighbor bone voxels; and
attenuation correct a plurality of positron emission tomography (PET) emission data using the MR-derived PET attenuation correction factors.

9. The medical imaging system of claim 8, wherein the computer is further programmed to perform an intensity based segmentation of the MR image dataset to identify the bone.

10. The medical imaging system of claim 8, wherein the computer is further programmed to:
compare the object to a plurality of images in an atlas; and
classify the bone based on the comparison.

11. The medical imaging system of claim 8, wherein the computer is further programmed to:
assign a first label map value to voxels representing bone; and
assign a second label map value to voxels that are not bone.

12. The medical imaging system of claim 8, wherein the computer is further programmed to:
identify a reference bone voxel in the MR image dataset;
count a number and distribution of connecting bone voxels for the reference bone voxel; and
generate a MR-derived PET attenuation correction factor scaling for the reference bone voxel based on the number of connecting bone voxels and neighbor bone voxels.

13. The medical imaging system of claim 8, wherein the computer is further programmed to:
assign a label map value to voxels representing bone;
identify neighbor voxels and a distribution of the neighbor voxels having the same label map value as a reference bone voxel; and
generate a MR-derived PET attenuation correction factor scaling for the reference bone voxel based on the number of neighbor bone voxels.

14. The medical imaging system of claim 8, wherein the computer is further programmed to:
determine a number and distribution of connecting bone voxels around a reference bone voxel; and
generate the MR-derived PET attenuation correction factors based on the determined number and distribution of connecting bone voxels and neighbor bone voxels.

15. A non-transitory computer readable medium encoded with a program programmed to instruct a computer to:
obtain a magnetic resonance (MR) image dataset;
classify at least one object in the MR image as a bone;
identify a reference bone voxel in the MR image dataset;
count a number of neighbor bone voxels for the reference bone voxel;
generate a MR-derived PET attenuation correction factor for the reference bone voxel based on the number of neighbor bone voxels; and
attenuation correct a plurality of positron emission tomography (PET) emission data using the MR-derived PET attenuation correction factors.

16. The non-transitory computer readable medium of claim 15, wherein the program is further programmed to instruct the computer to perform an intensity based segmentation of the MR image dataset to identify the bone.

17. The non-transitory computer readable medium of claim 15, wherein the program is further programmed to instruct the computer to:
compare the object to a plurality of images in an atlas; and
classify the bone based on the comparison.

18. The non-transitory computer readable medium of claim 15, wherein the program is further programmed to instruct the computer to:
assign a first label map value to voxels representing bone; and
assign a second label map value to voxels that are not bone.

19. The non-transitory computer readable medium of claim 15, wherein the program is further programmed to instruct the computer to:
identify a reference bone voxel in the MR image dataset;
count a number and distribution of neighbor bone voxels for the reference bone voxel; and
generate a MR-derived PET attenuation correction factor scaling for the reference bone voxel based on the number of neighbor bone voxels.

20. The non-transitory computer readable medium of claim 15, wherein the program is further programmed to instruct the computer to:
determine a number and distribution of neighbor bone voxels around a reference bone voxel; and
generate the MR-derived PET attenuation correction factors based on the determined number of neighbor bone voxels.

* * * * *